United States Patent [19]
Cruz

[11] Patent Number: 5,954,678
[45] Date of Patent: *Sep. 21, 1999

[54] ORTHOSIS FOR AN ANATOMICAL JOINT

[76] Inventor: Mark Cruz, P.O. Box 91, Caldwell, N.J. 07006

[*] Notice: This patent is subject to a terminal disclaimer.

[21] Appl. No.: 08/917,250

[22] Filed: Aug. 25, 1997

[51] Int. Cl.⁶ .................................................. A61F 5/00
[52] U.S. Cl. ............................................. 602/26; 602/16
[58] Field of Search ................... 602/5, 16, 20, 602/23, 26; 601/33, 34

[56] References Cited

U.S. PATENT DOCUMENTS

| | | | |
|---|---|---|---|
| 5,297,294 | 3/1994 | Washick | 602/16 X |
| 5,466,192 | 11/1995 | Castolo et al. | 602/16 X |
| 5,653,680 | 8/1997 | Cruz | 602/16 X |
| 5,662,595 | 9/1997 | Chesher et al. | 602/16 X |
| 5,669,873 | 9/1997 | Towsley | 602/16 X |
| 5,685,830 | 11/1997 | Bonutti | 602/16 |

*Primary Examiner*—Linda C.M. Dvorak

[57] ABSTRACT

The novel elbow/knee orthosis is designed to rigidly hold the joint in any position throughout the entire range of motion of the joint, and is able to apply a force to urge the joint into flexion or extension, all within a single embodiment. The orthosis is low profile, light weight, easily fitted and removed, and is specifically designed for pediatric applications.

6 Claims, 3 Drawing Sheets

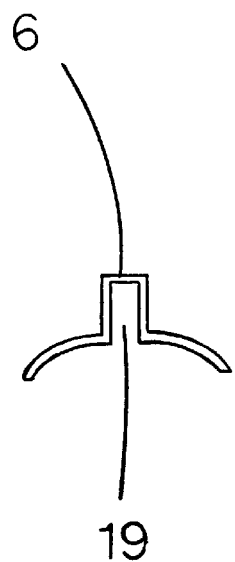 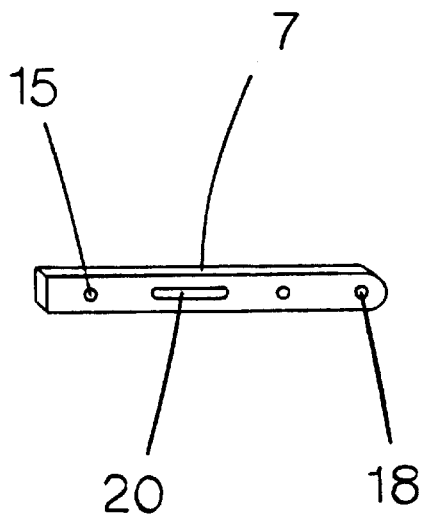
FIG. 3
FIG. 4

ORTHOSIS FOR AN ANATOMICAL JOINT

RELATED ART

The mandate for this invention stems from an evolving approach to treating joint trauma due to fractures, neurological disorders and disease, and particularly, for treating children from six months of age on up. In addition to the short-comings of the existing technology, all prior orthosis are designed for adults and, typically, would not be scaled down, effectively, to fit children under age 8. This invention is specifically designed for pediatrics and smaller applications.

An example of existing treatment in a typical joint injury is this: after the trauma or surgery the joint is immobilized in a rigid cast for weeks or months. Then, when the cast is removed, the joint is stiff, has limited range of motion, and the patient is sent to a therapist. Through repeated force, stretching and exercise, the therapist tries to increase the range of motion to an acceptable range. This takes months, and typically the patient regains only limited range of motion. After all else has failed, then, the therapist generally requests an external orthosis that can apply low-load, long-duration force to the joint. Unfortunately, so much time has passed by this point the joint is much harder to rehabilitate.

The new school of thought on joint trauma treatment is this: after a shorter initial immobilization period, it is more beneficial, and results in less joint stiffness, if the joint is allowed to have a small, ever increasing range of motion. The joint can be mobilized, in this ever increasing range of motion, through a low-load, long-duration force. While this is taking place, it is still important to support, protect, and hold the joint securely so that movement is limited to the desired range only. No current art is designed for this broad treatment application and none are specifically designed for pediatrics in the aforesaid new treatment.

A further example for an application of this invention is a newborn with disease causing an elbow to retract to the flexed position. Typical current therapy may involve extending and strapping the arm to a rigid splint to hold it, to try to fight and re-train the muscles. This results in no movement of the joint, or limited movement within the splint, resulting in further stiffening complications. A more desirable treatment would be to hold the joint extended with a selected force, and yet to allow the joint to be flexed against this force, the more the joint is flexed, the more it encounters resistive force.

No prior orthosis can, in the same brace, provide an adjustable static splint throughout the entire range of motion, a dynamic flexion or extension force, and provide dynamic flexion or extension resistance. None can go from a full-range static splint, to a dynamic rehabilitation aid without serious transformation, most can't do it at all. None are as light weight and uncomplicated as my invention. None can provide low lateral profile with no exposed components. None are suitable for pediatrics. None are simple to apply and remove. This invention is held on with only two straps, and meets all these goals.

Prior art at best can provide a bulky, heavy, complex brace/orthosis/splint that provides force to the joint in one deviation only, either flexion or extension, and none are suited for newborns and pediatrics. The best example of a prior art device is Mauldin, in his U.S. Pat. No. 4,370,977, he simply attaches a spring between a pivotal splint to urge the elbow into flexion. His invention is bulky, provides no extension force, cannot rigidly splint, and would never be suited for pediatrics. My invention solves all these problems.

SUMMARY OF THE INVENTION

The present invention, a prefabricated, dynamic, interactive knee or elbow orthosis is a simple, low profile, light weight, easily adjustable external orthosis. It applies low load, long duration force and resistance to the knee or elbow in flexion and extension. The orthosis is dynamic and, without any modifications, can go from a static rigid splint; to a splint with limited ranges of motion; to an active or reactive rehabilitation aid providing dynamic force or resistance to the joint in both deviations.

The invention consists of an upper leg and lower leg or arm cuffs, constructed from thermoplastic, lined with foam, linked together on either side with flexible, plastic, tube-type, or low profile plastic pivot joints, and is held to the arm or leg with typical hook and loop strap fasteners.

Mounted perpendicular to the pivot of the joint, in line with the arm or leg, on the back side of one of the two cuffs, on the dorsal side of the leg or arm, is housing containing a slidable link. The housing has a plurality of holes in it and the link has at least one hole in it. Said link may be extended or retracted and may be locked by lining up the hole in the link with any hole in the housing and inserting a thumb screw or pin.

Pivotably attached to the front of the link is a threaded rod. Mounted on the back side of the other cuff piece is vertically disposed tab with a hole in it. Said rod travels through the hole in the tab and has thumb knobs on either side of the tab. A spring may be added to the rod on either side of the tab between it and a thumb screw.

The reciprocal link, housing, and spring loaded rod assembly are covered with a foam boot or other flexible protective cover. There are no exposed components other than the smooth plastic cuff pieces, and smooth, low profile hinges. The foam boot is not depicted in this application for simplicity.

OBJECTS OF THE INVENTION

An object of this invention is to provide a light weight, low side profile dynamic orthosis for infants, pediatrics and young adult patients.

Another object of this orthosis is to provide easy application and simple operation with no tools or different embodiments necessary to use all the features of this orthosis.

A further object of this knee and elbow orthosis is to provide a fully adjustable static or static/dynamic splint, a splint that is able to rigidly hold the elbow or knee in any position of its normal range of motion.

One other object of this orthosis is to allow yet resist an adjustable range of motion in flexion and extension.

A further object is to be able to apply a force while limiting, blocking, or allowing a range of motion.

Another object of this invention is to provide incremental force to the knee or elbow in flexion and extension.

Yet another object of this invention is to support and protect the injured elbow or knee joint.

Too, an object is to accomplish all the aforementioned goals in a single embodiment.

More specifically, it is and object of this invention to set forth an orthosis for an anatomical joint comprising first means for releasably clasping a first anatomical member; second for means releasably clasping a second anatomical member; means coupled to both first and second means for pivotably joining said first and second means together; and means mounted upon said first and second means operative for controlling pivotable motion between said first and second means.

BRIEF DESCRIPTION OF THE DRAWINGS

Further objects of this invention, as well as the novel features thereof, will become apparent by reference to the following figures, in which:

FIG. 3 is an end view of the linkage housing;

FIG. 4 is a perspective view of the linkage.

DETAILED DESCRIPTION OF THE INVENTION

Figure 1:
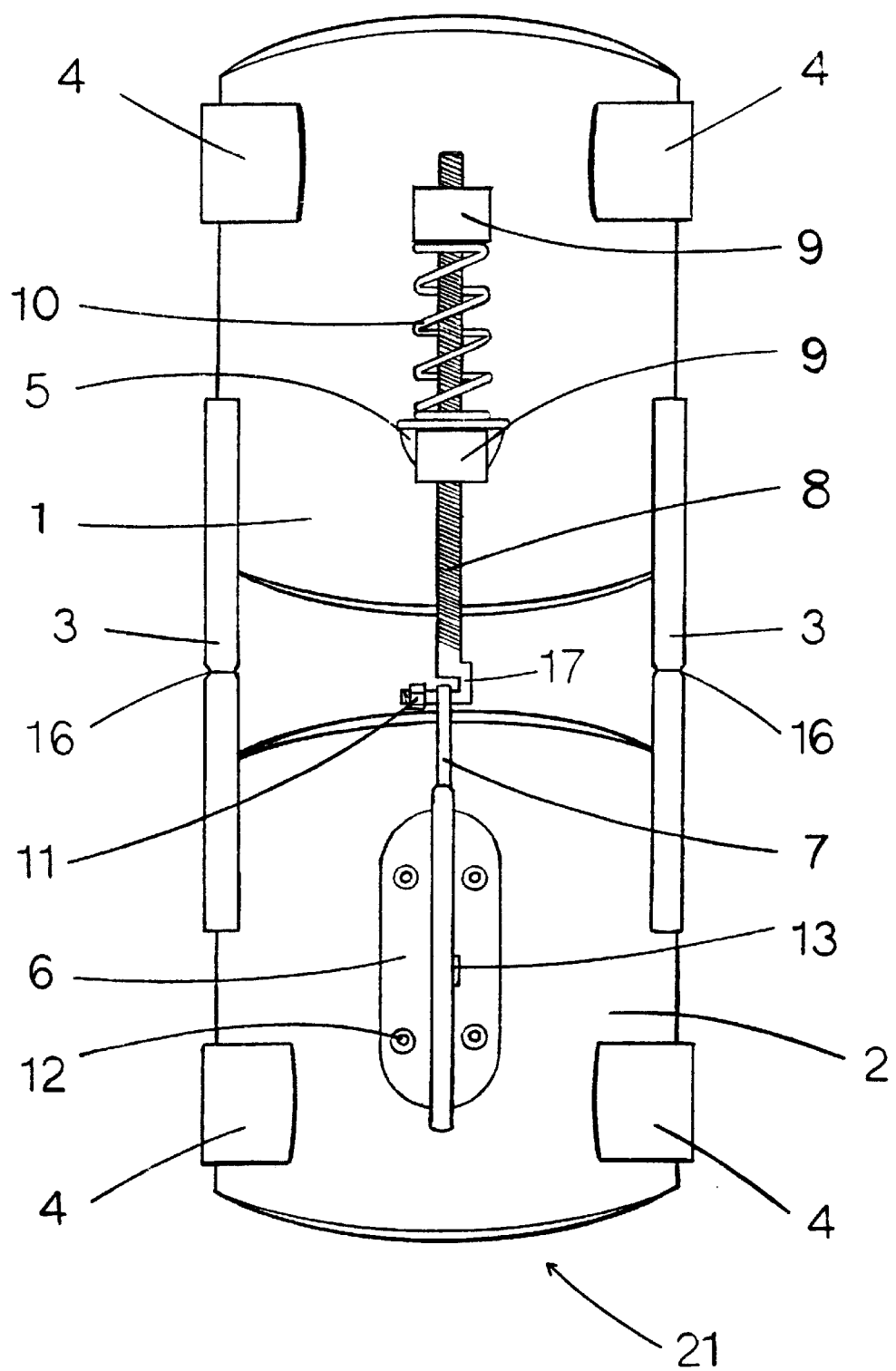
FIG. 1 is a top, plan view of the novel orthosis, according to an embodiment thereof.
Figure 2:
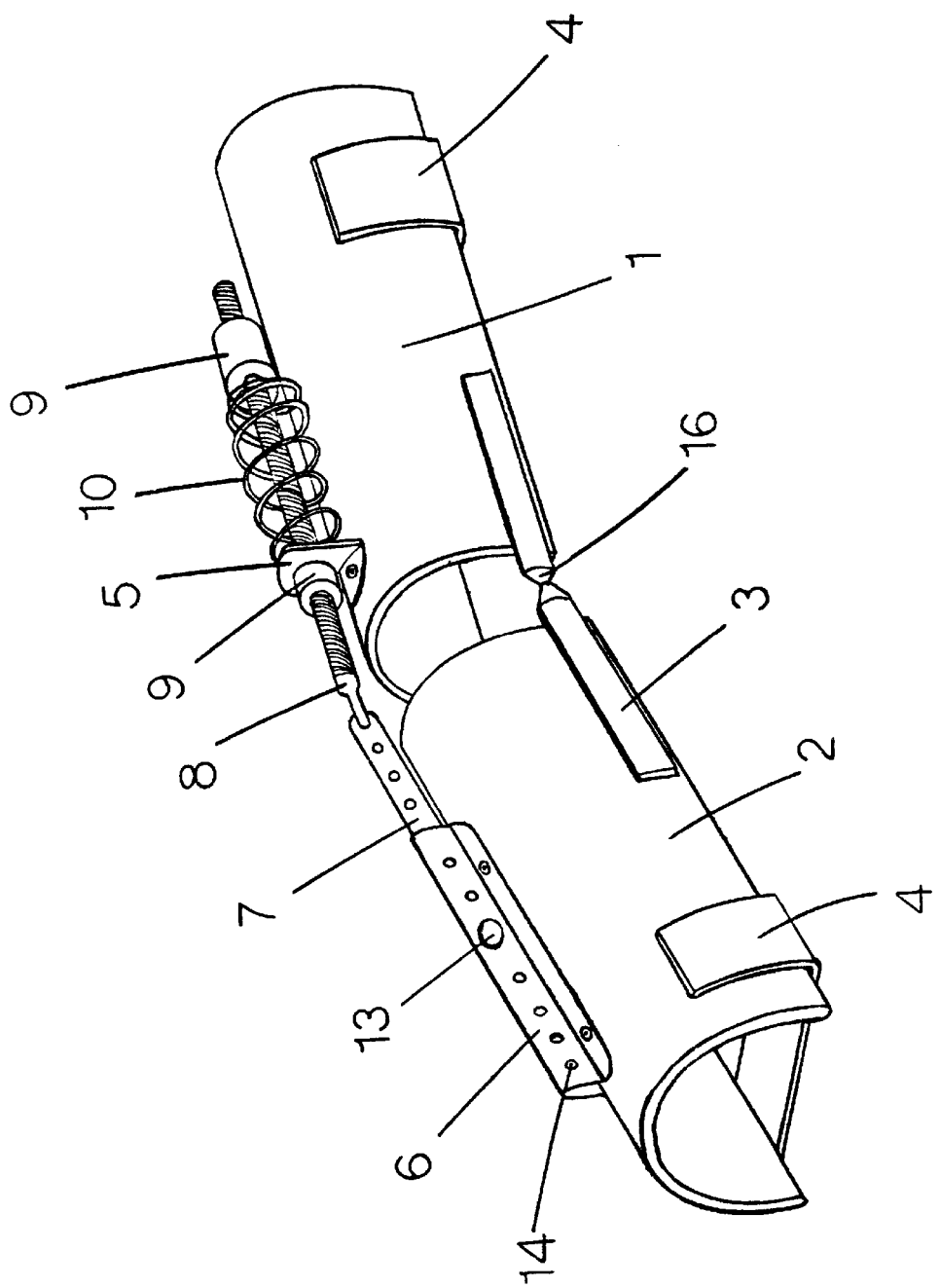
FIG. 2 is a perspective illustration thereof.

The inventive orthosis as shown in FIG. 1 and FIG. 2 comprises two thermoplastic or like material cuffs 1 and 2, that are lined with foam and curved to fit the dorsal surface of the arm or leg. These cuffs are held in place with typical hook and loop strapping 4.

These cuffs 1 and 2 are linked together on the sides in line with the pivot of the joint by plastic tubes 3 that are flattened on their sides and crimped in the center 16 to form hinges. It would be possible to substitute other hinge assemblies however the tubes offer the lightest weight, lowest cost and simplest operation. These tubes are fastened to the cuffs by glue and/or rivets.

Mounted on cuff 1 is an apertured tab 5. The tab is made of aircraft grade aluminum and is riveted to said cuff. Slidably engaged through the aperture in the tab 5 is a threaded rod 8. The rod has two threadedly engaged thumb screws 9 and a spring 10 mounted upon it. The spring 10 rides between the tab 5 and one thumb screw 9 and results in a spring loaded rod assembly. The spring 10 may be fitted on either side of the tab 5 thereby being able to provide force to the other cuff 2 in either direction dependent on which side the spring 10 is mounted. At the end of the rod 8 facing the other cuff 2 is a bent or formed end 17 designed to fit in an end hole 18 of shaft 7. The tip of the bent or formed end 17 is threaded and receives a nut 11 to hold it in place.

Mounted atop the other cuff 2 is an apertured housing 6. The housing comprises a channel 19. The housing 6 is held in place with rivets 12 or like fasteners. Slidably engaged within the housing 6 is a link 7 made of nylon or like plastic. The housing 6 and linkage 7 are shown enlarged in FIG. 3 and FIG. 4. The link 7 has a plurality of holes 15 and a slot 20 that line up with the holes 14 in the housing 6. A plastic pin or clip 13 is inserted through any hole 14 in the housing 6 and a hole 15 in the link 7 thereby allowing an adjustable fixed length. By inserting pin 13 through any hole 14 in the housing and slot 20 in linkage 7 somewhat free flexure may be effected. Furthermore, by removing spring 10 and adjusting thumb screws 9 and linkage 7 any free flexure may be obtained.

Through placement of the spring 10, adjustment of the link 7 through holes 14, 15 and placement of the thumb screws 9 it is possible to: (1) statically splint throughout the range of the joint, and (2) limit or block out a range of motion while allowing an accompanying unrestricted or resisted range of motion, and, (3) to apply an adjustable force to the joint in flexion or extension throughout the entire range of motion, and (4) to apply an adjustable resistive force in flexion or extension throughout the entire range of motion and to do it all simply, quickly, and with no other tools or modifications necessary.

While not shown herein, the invention comprehends the use of protective covering for the novel orthosis. A protective boot, of foam composition, is used for emplacement over the housing 6, linkage 7, rod 8, thumb screws 9, and spring 10. With the boot in position there are no injury causing components exposed to the patient.

While I have described my invention in connection with a specific embodiment thereof, it is to be clearly understood that this is done only by way of example, and not as a limitation to the scope of the invention, as set forth in the objects thereof, and in the appended claims.

I claim:

1. An orthosis for an anatomical joint, comprising:

first means for releasably clasping a first anatomical member;

second means for releasably clasping a second anatomical member;

means coupled to both said first and second means for pivotably joining said first and second means together; and means mounted upon said first and second means operative for controlling pivotable motion between said first and second means; wherein said pivotable motion controlling means comprises a housing, with a linkage slidable within said housing, fixed to one of said first and second means, and an upstanding, apertured tab, with a spring loaded rod in slidable penetration of said tab and coupled to said linkage, fixed to the other of said first and second means.

2. An orthosis for an anatomical joint, according to claim 1, wherein:

said rod is threaded substantially throughout the full length thereof; and further including two thumb nuts threadedly engaged with said rod on either side of said tab; and a compression spring disposed about said rod, with one spring end set against a given side of said tab; wherein at least one of said thumb nuts on said rod is engaged with the other end of said spring; and said other thumb nut is positioned on the other side of said tab from which the spring is set.

3. An orthosis for an anatomical joint, according to claim 1, wherein:

said linkage comprises an elongate link having (a) at least one aperture formed therein, and (b) a longitudinal slot formed therein; and said housing has a plurality of holes formed therein for alignment with at least one aperture in said link.

4. An orthosis for an anatomical joint, according to claim 1, wherein:

said pivotable motion controlling means further comprises means for (a) facilitating pivotable movement between said first and second means, (b) resisting pivotable movement between said first and second means, and (c) prohibiting all movement between said first and second means.

5. An orthosis for an anatomical joint, according to claim 1, wherein:

said housing and said linkage have means mutually cooperative for (a) prohibiting movement of said linkage within said housing, and (b) limiting movement of said linkage within said housing.

6. An orthosis for an anatomical joint, according to claim 1, further including:

means mounted on said rod manipulative for selectively adjusting the bias of said spring.

* * * * *